United States Patent [19]

Haas et al.

[11] Patent Number: 5,143,696
[45] Date of Patent: Sep. 1, 1992

[54] SELECTIVE GAS SENSOR

[75] Inventors: Juergen Haas, Meersburg; Carsten Plog, Markdorf, both of Fed. Rep. of Germany

[73] Assignee: Dornier GmbH, Friedrichshafen, Fed. Rep. of Germany

[21] Appl. No.: 605,511

[22] Filed: Oct. 30, 1990

[30] Foreign Application Priority Data

Nov. 4, 1989 [DE] Fed. Rep. of Germany ....... 3936758

[51] Int. Cl.$^5$ ...................... G01N 27/00; G01N 27/04
[52] U.S. Cl. ........................................ 422/90; 422/98; 324/663
[58] Field of Search .................. 73/23.3; 324/663; 422/90, 98; 361/286

[56] References Cited

U.S. PATENT DOCUMENTS

| 4,164,868 | 8/1979 | Suntola | 361/286 |
| 4,453,151 | 6/1984 | Leary et al. | 422/90 |
| 4,564,882 | 1/1986 | Baxter et al. | 361/286 |
| 4,654,624 | 3/1987 | Hagan et al. | 422/98 |
| 4,795,968 | 1/1989 | Madou et al. | 422/90 |
| 4,892,834 | 1/1990 | Rauh | 422/98 |
| 4,893,214 | 1/1990 | Nishiwak et al. | 361/286 |

*Primary Examiner*—Robert J. Warden
*Assistant Examiner*—T. A. Trembley
*Attorney, Agent, or Firm*—R. H. Siegemund

[57] ABSTRACT

A sensor for selective determination of gases includes an electric capacitor having a gas permeable zeolite layer between 2 and 500 micrometer thick and being composed of a dielectric crystalline structure with a crystal size from 0.1 micrometer to 80 micrometer and having primary pores resulting in an internal surface from 100 to 1500 m$^2$/g, the diameter of the pores being between 0.1 and 1.5 nm which corresponds at least in order to magnitude to the kinetic diameter of the molecules of the gas to be detected, so that these molecules penetrate deep into the layer and its pores thereby changing the dielectric constant of the layer.

15 Claims, 2 Drawing Sheets

DYNAMIC BEHAVIOR AT 280°C
4000 ppm BUTANE

SELECTIVE GAS SENSOR

BACKGROUND OF THE INVENTION

The present invention relates to a selectively operating, chemical gas sensor which includes as its main active element a capacitor with a dielectric material in between the electrodes which layer is constituted by a gas permeable layer.

Many instances of automated processes require the utilization of many relatively simple, small and economic measuring transducers and associated devices. This is particularly important concerning the measurement of contaminants and contaminate emissions. The demand for equipment along this line is in fact increasing with the growing import of ecologically safe manufacturing and other facilities. In connection therewith certain transducers have been developed that acquire a chemical quantity, such as the concentration of a particular material, and provide a measuring result provided of course it is physically possible to obtain and actually acquire a reasonable and reasonably reliable measuring quantity. The measured item is converted so to speak by the transducer into an electrical signal such as a current or an electrical voltage (or both).

Transducers of the kind referred to above are generally called chemical sensors. They of course involve an indirect measuring method which on the other hand carries with it the problem of selectivity and transverse sensitivity. As compared with physical sensors these particular parameters of chemical sensors are comparatively low.

Generally speaking chemical sensors are constructed to have some form of gas sensitive layer and a carrying transducer element for other components and which together constitute the transducer proper. The electrical converting element may be in an oscillating quartz. Moreover, the device will include interdigital capacitors, FET-s and the like. The transducer proper (other than the sensitive layer) is not chemically sensitive but the transducer has an input structure including the gas sensitive layer that converts the chemical parameter into another physical quantity which in turn is then converted into an electrical parameter. The effect of course is basically an interaction between the environment to which the device is exposed on one hand and the aforementioned chemically sensitive layer.

Electrically insulating gas selective coatings are provided on microstructure element in the following fashion. So called organically modified silicates (also ormosiles) are used as a selectively active, adsorber structure and the coating is comprised of an amorphic skeleton to support a molecular frame under utilization of siloxane compounds (Si—O—Si) which acts in an analogous fashion to anargonic skeleton silicates. The specifically effective adsorption of gas molecules is provided through functionally organic groups. The physical-chemical measuring effect now resides in the change of the dielectric constant in and of whatever layer is used on account of the adsorption process involving whatever is being picked up from the environment. However, it is apparent that adsorption obtains only in the surface and therefore the sensitivity of such an ormosile layering is quite low.

The manufacture of monomolecular coatings on microstructures components use the following technology developed by Langmuir and Blodgett. A film is provided (floating) on top of a water surface, the film being constituted by elongated molecules and the water is used just as carrier. This film is then deposited on the microstructure surface and construction element. First tests here were made under utilization of phtalocyanines. This material has a known adsorption capability as far as NO molecules are concerned. However, through variation of the central molecule in this phthalocyanine complex one can render the sensor sensitive to other molecules.

Still another method involves tin oxide layers which are provided by operation of vacuum depositing and cathode sputtering. This concept deposits thin polycrystalline tin oxide layers on an insulating carrier. Suitable metallizing is provided in addition for obtaining the requisite electrodes. These elements are heated up to 300 to 400 degrees C in order to obtain an interaction between gas of the environment and the particular sensitive layer. Under participation of reducing gases the layer modifies its conductivity as a function of gas concentration. However, a significant problem of this device arise from its inadequate selectivity as well as lack of stability of the layer involved.

Independently from the foregoing tests have been conducted for using zeolite as a filter for coating of FET-s. Their effect is supposed to be based on the different and selective permeability of the zeolite for differing gases. However, significant problems have resulted on account of the diffusion of gases through so called secondary pores that exist right at the gates of the FET. This diffusion in fact eliminates selective operation of these devices.

DESCRIPTION OF THE INVENTION

It is an object of the present invention to provide a new and improved selectively operated chemical sensor for gases of the type alluded to above and being comprised of a capacitor as the essential pick-up element having a dielectric material that is permeable to gas.

It is a specific object of the present invention to provide for a more sensitive coating of microelectronic components that obtain this way a selectivity for certain gases and here it is a feature that used to be made primarily of selective dimensioning of primary pores under avoiding of interfering effects through secondary pores.

It was found that the problem of gas diffusion through secondary pores under utilization of chemically sensitive layers of zeolite in connection with a capacitor structure can be solved in an advantageous manner. The sensitive layer is comprised from 50% to 100% of zeolite. The zeolite layer has a crystal structure with pores and ducts and channels of a diameter between 0.1 and 1.5 nm. Here one does not depend on the filter effect of a zeolite layer as far as a FET is concerned being so to speak upstream on a chemically sensitive layer, but the zeolite layer itself becomes the chemically sensitive layer. The latter phenomenon results from either zeolite or another material with a crystal structure such that pores have a diameter that is comparable at least in order of magnitude with the size of the molecules of the gas to be detected. The primary pores are to be between 0.1 and 1.5 nm.

Essential for the measuring effect in conjunction with the capacitor structure is the amount of gas adsorbed within the zeolite crystals. This way one makes full use of the form selective effect of the zeolite because only molecules having a gas kinetical diameters not larger than the pore sizes within the zeolite can pass by diffusion. The diameter of the primary pores which are internal crystallite channels and cavities of the particular zeolite, should be advantageously comparable, at least in order of magnitude, to the gas kinetic diameter of the molecules to be detected in the first place. The amount of the material constituting the adsorbing layer at the outer zeolite surface or at the capacitor structure itself is only of secondary importance.

In a particular configuration the system of zeolite and capacitor may use the form selective property of the zeolite as far as catalytic gas reactions are concerned. The inclusion of oxidizing active metals in the zeolite pores through known methods such as ion exchange or adsorption of metal vapors or of volatile metal compounds, and a subsequent thermal or thermally reducing treatment provides for an oxidizing of only those molecules that diffuse into the zeolite pores. This effect modifies significantly the capacitance of the capacitor.

Contrary to the layering of capacitor structures with gas permeable layers wherein owing to the system involved there is available only a very thin layer and therefore a low sensitivity, the configuration of the sensitive zeolite crystal layer as per the invention makes use of fast diffusion of the gas molecules through the secondary pores. This aspect permits employment of a larger layer thickness and therefore and increase in the sensitivity. Layer thicknesses from up to 100 micrometers and even more can be realized without significant loss in response time and speed. The crystal size of the zeolite primary particles should be between 0.1 and 80 micrometers.

The following properties are deemed relevant as far as the zeolite use in the sensitive layer. First of all there is a well defined pore volume covering the range of gas kinetic diameters of many molecules that are of interest as far as measurements are concerned. In addition zeolite the sum total of all of the internal pore surface areas in the zeolite is very large such as from 100 to 1500 $m^2/g$. In some applications the catalytic activity is very high. Moreover these layers are quite stable under various temperature conditions. In principle one can use all known zeolite types such as faujasite, mordenite, pentasile etc. Analogous zeolite compounds can be used such as ALPO or SAPO.

In order to obtain catalytically oxidizing effects zeolites are preferably doped with metal of the platinum group which includes Pt, Pd, and Rh. Here elemental or ionic metal may be provided in the zeolite; or one uses an oxide or clusters. In order to utilize adsorption effects, the material may be doped with metals of side groups of the periodic systems such as copper, nickel, iron, cobalt, vanadium, chromium, manganese or silver. Again, these metals may be present in elemental form, ionically, as oxides or as clusters.

In conjunction with and as part of the transducer, the chemically sensitive layer can be used in conjunction with different kinds of capacitors and capacitively operating transducers. It is only required that they provide an interaction of the sensitive layer with the surrounding gas atmosphere and that a change in dielectric constant obtains which establishes in turn a sufficiently noticeable, recognizable and detectable effect on the capacitance(s) in the measuring device. One will use microstructured capacitors with interdigitized electrodes, because one can readily obtain a basic capacitance within a very small space.

Interdigitized capacitors can be manufactured through the usual microstructure processes. For example, NiCr/Ag may be sputtered onto a quartz substrate with subsequent structuring by means of etching. These structures are between 1 and 100 micrometers wide with an electrode height up to about 2 micrometers. This basic capacitor is then provided with the chemically active zeolite layer by means of sedimentation, spraying, centrifugally depositing of spinning and other known processes of thick layer depositing. The chemically sensitive layer that results is to be between 2 micrometers and 500 micrometers thick.

A high aspect ratio of the capacitor structure in conjunction with the highly porous, chemically sensitive layer results in a drastic increase in detection sensitivity. For thicker electrodes, in excess of 2 micrometers, the structure is called a 3D interdigitized capacitor. The three dimensional aspect is readily usable in conjunction with the highly porous chemically sensitive layer. Owing to the pore size requirement, the measuring gas can penetrate and diffuse deeply into a fairly thick chemically sensitive layer. Hence, adsorption and other chemical action will be observed throughout that layer and not just on the surface. The sensitivity is increased because the measuring effect is produced by action in the space directly between the electrodes.

The 3D interdigitized capacitor can be made quite analogous to the planar one. What is involved is an increase in thickness of the electrodes with commensurate increase in the layer thickness of the chemically active dielectric. The electrode thickness may be increased galvanically, i.e. through electrolytic depositing above the 2 micrometers level, up to about 100 micrometers. The width of the electrodes remains between 1 micrometer and 100 micrometer. The chemically sensitive porous layer is then deposited just as before, at the requisite thickness such that the electrodes remain always embedded in zeolite.

Through modifying the chemically sensitive layer as far as catalytic activity and selectivity is concerned as well as by introducing certain special adsorption centers and well defined pore diameters one can use these inventive capacitive sensors, as so coated, in conjunction with the detection of a large number of gases, such as all kinds of hydrocarbons; halogenic hydrocarbons; CO;NO, ammonia, H2O etc. Advantage is taken of a very short response time, of a high selectivity and/or minimized transverse sensitivity as can be derived from the figures.

BRIEF DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Generally speaking, the invention is particularly suitable for detecting gas components having small molecules, such as ammonia, NO, NO2, CO and water, because hydrocarbons and halogenic carbons can be detected.

Figure 1:
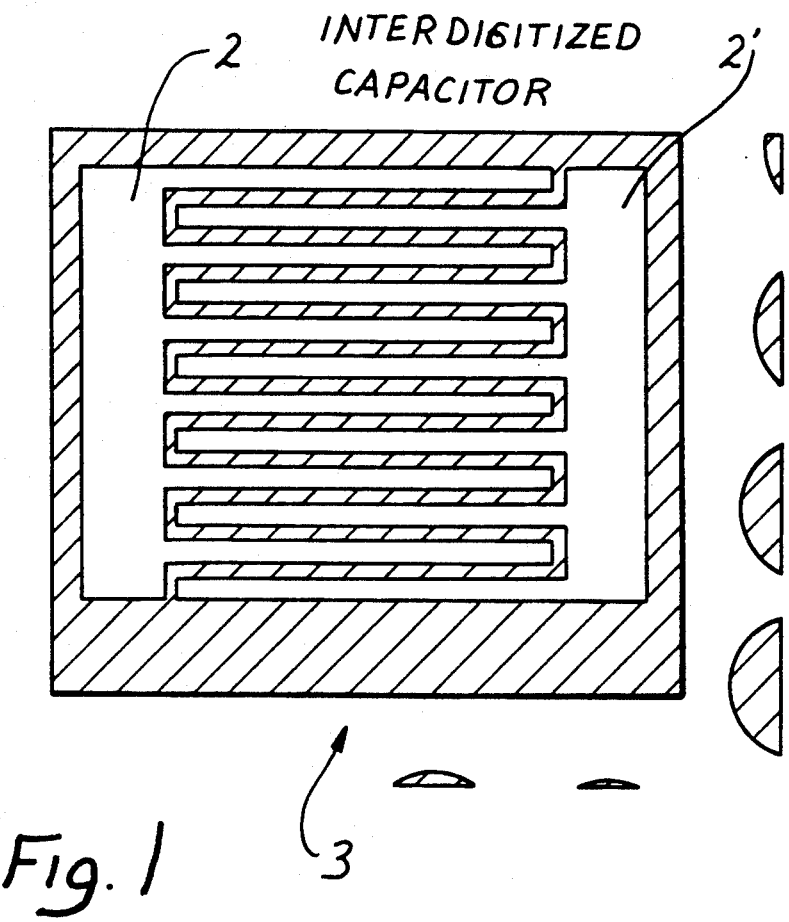
FIG. 1 illustrates a top view of an interdigitized capacitor.
Figure 2:
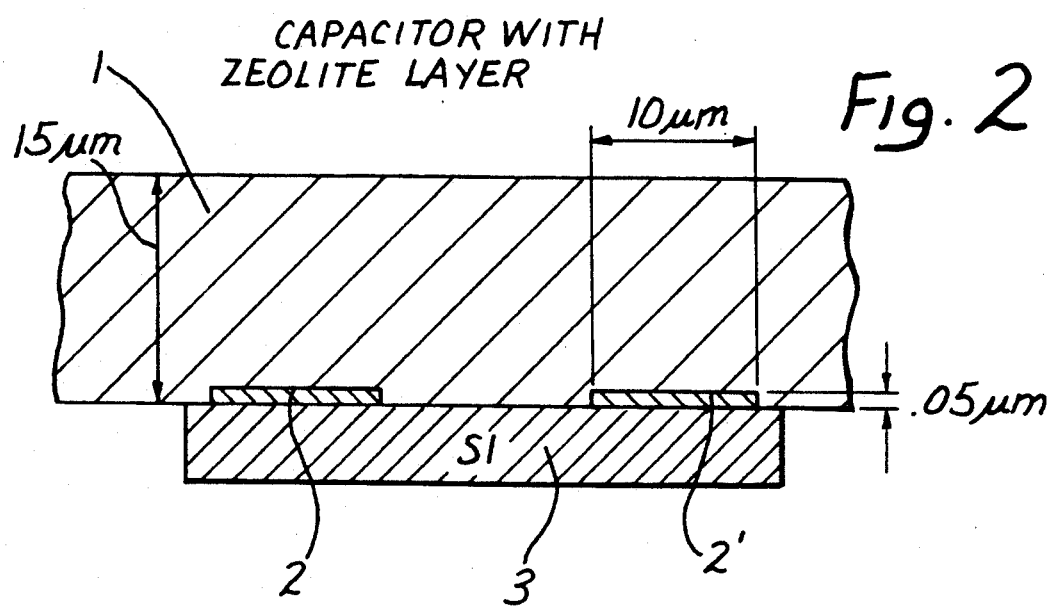
FIG. 2 illustrates a cross section through the interdigital capacitor shown in FIG. 1.

Proceeding now to the detailed description of the drawings, FIG. 1 is more or less self explanatory. It includes two interdigitized electrodes 2 and 2' separated by space between them, the zeolite layer has been peeled away for the illustration. The various electrodes are about 100 micrometers wide. FIG. 2 shows a silicon carrier 3 with the conductor layers 2 and 2' made of aluminum providing for the requisite electrode operation and reference numeral 1 refers to a 15 micrometer thick layer of zeolite made in accordance with one of the methods of this invention. This configuration is of a general nature. One can use the comb-structure of FIG. 1 or a spiral-concentric arrangement of the electrodes.

Figure 3:
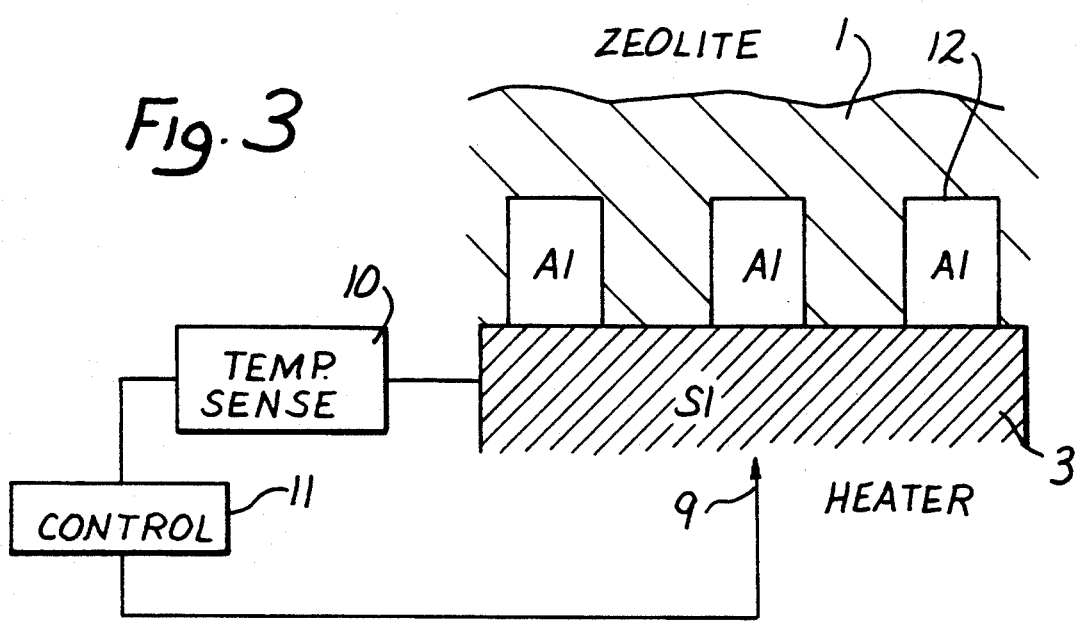
FIG. 3 illustrates a cross section through a 3D device.

The capacitor shown in partial cross-section in FIG. 3 shows much higher aluminum electrodes 12, all other compounds are the same as those in FIG. 2. FIG. 3 shows also a heater 9 for the transducer wafer, a temperature sensor 10 which is connected to a controller which in turn controls the heater 9. The same temperature control can of course be provided for the low height configuration of FIG. 2. Generally, the operating temperature will be between 10 and 500 degrees C.

Proceeding now to further detail we first refer to manufacture of the zeolite layer and we begin with the making of a zeolite powder. For this it is suggested to use 20 g of sodium-Y zeolite, which is ion-exchanged under utilization of a back flow of a 0.8 l ammonium nitrate solution. The treatment was run three times for 24 hours whereby in between the material was subjected to filtering, and the filter cake was washed in each instance in hot water. Subsequently the resulting zeolite powder was dried and temperature treated.

Beginning with the zeolite powder as so made a Pt-Y zeolite is made through ion exchange under utilization of [Pt(NH$_3$)$_4$]Cl$_2$ in a watery solution. For 24 hours material was stirred at room temperature using rather little water. Following filtering and washing the filter cake it was dried and again subjected to a temperature treatment. For making elementary platinum the zeolite was reduced in a stream of hydrogen.

Turning now to the production of the gas sensor itself for example of the kind shown in FIGS. 1, 2 an interdigitized capacitor, or IDC for short was used as shown in FIGS. 1, 2 with aluminum conductor electrodes on a silicon-silicon dioxide wafer base. The structure was about 15 micrometers thick. The IDC was fixed with a temperature proof bonding adhesive and bonded onto base. The zeolite layer was then deposited through sputtering a watery suspension as the powder had been made under concurrent evaporation of water. Depending on the duration of spraying and sputtering the thickness of zeolite layer was determined to have actually grown to about a 15 micrometer thickness level as already stated earlier.

The device was then tested in a laboratory test using butane at 50 degrees C. The sensors here were particularly investigated with regard to the production of signals; for this, the measuring chamber was flown through by synthetic air at a rate of 2 liters per minute, for carrying a well defined amount and concentration of the component to be measured. The temperature was maintained at 50 degrees C and for the component "butane" the following results were obtained.

TABLE 1

| zeolite | Pore width | capacitive differential for 1.2 Vol.-% butane |
|---|---|---|
| H-zeolite | 0.74 nm | 2.48 pF |
| H-zeolite | 0.55 nm | 0.25 pF |
| H-zeolite | 0.39 nm | 0.18 pF |

Next, laboratory tests were conducted in order to obtain information about the selectivity on one hand and the transverse sensitivity, at 50 degrees C on the other hand. The tests were conducted analogously using ethane or carbon monoxide instead of butane. These tests did not result into any significant production of a signal by the particular sensor!

Next, a lab test was conducted for butane at 200 degrees C, using a PT doped zeolite as a sensitive layer. The following results for various frequencies were obtained in terms of measured capacitive differential delta C in picofarads.

TABLE 2

| Frequency (Hz) | delta C (pF) for 1 Vol.-% butane |
|---|---|
| 500 | 8.0 |
| 600 | 9.0 |
| 800 | 9.0 |
| 1000 | 8.9 |
| 1200 | 8.6 |
| 1500 | 8.5 |
| 2000 | 8.0 |
| 2500 | 7.6 |
| 3000 | 7.3 |
| 4000 | 6.5 |
| 5000 | 5.9 |
| 6000 | 5.4 |
| 8000 | 4.5 |

Next, a lab test was conducted with dichloromethane at 60 degrees C, and the following results were obtained.

TABLE 3

| Zeolite | Pore width | delta C for 1 Vo.-% dichloromethane |
|---|---|---|
| H-Zeolite | 0.74 nm | 0.18 pF |
| H-Zeolite | 0.55 nm | 0.64 pF |
| H-Zeolite | 0.39 nm | 0.61 pF |

Figure 4:
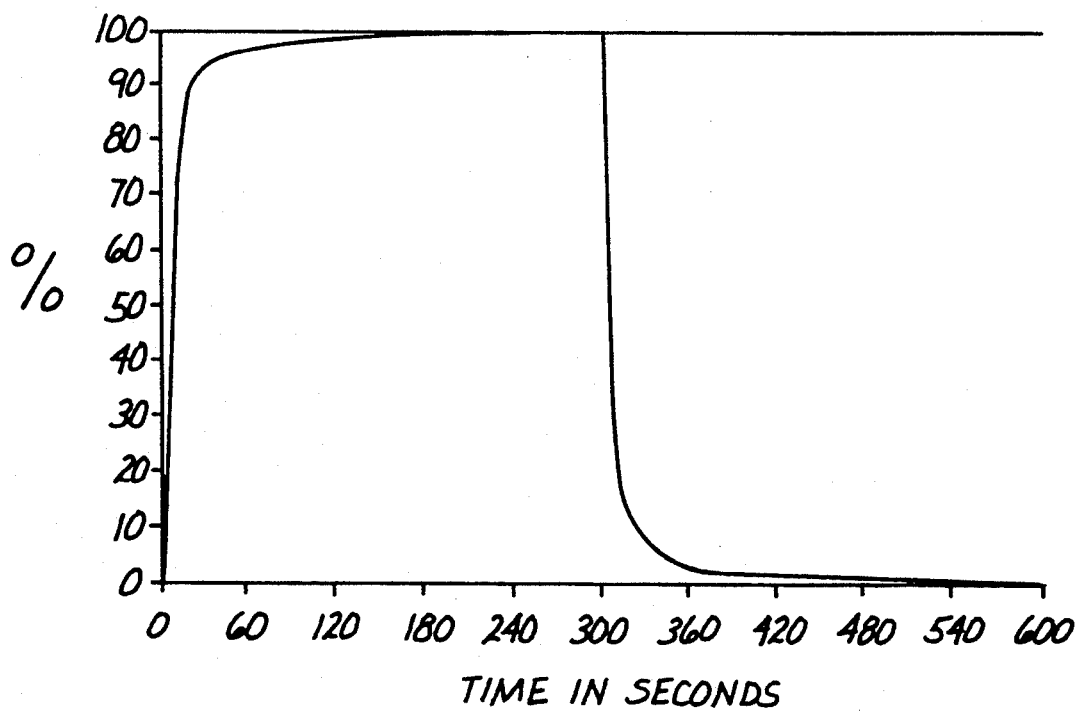
FIG. 4 illustrates a diagram of such a capacitor as far as response time and decay is concerned.

In order to measure response as well as decay for the gas sensor the carrier gas was modified by adding 4000 ppm butane at 280 degrees C in form of step function. That concentration was maintained for a particular period of time and then removed from the flow-through gas in the same rapid fashion. As shown in FIG. 4 the sensor did indeed react very quickly. Within 15 to 20 sec the 90% of the final values was reached and the signal remained stable. Analogously as the adding of butane was interrupted the sensor needed only about 100 sec before returning to a near zero value.

The invention is not limited to the embodiments described above but all changes and modifications thereof, not constituting departures from the spirit and scope of the invention, are intended to be included.

We claim:

1. In a sensor for selective determination of gases which includes an electric capacitor with a gas permeable sensitive layer serving as a dielectric, wherein the improvement comprises:

the gas permeable sensitive layer being composed of an ordered crystalline structure having primary pores, the diameter of which corresponds at least in order to magnitude to the kinetically effective diameter of molecules of a gas to be detected, so that these molecules penetrate deeply into secondary pores of the gas permeable sensitive layer by diffusion thereby changing the dielectric constant of the gas permeable sensitive layer.

2. Sensor in accordance with claim 1, wherein the gas permeable sensitive layer is between 2 and 500 micrometers thick.

3. Sensor as in claim 1, wherein the gas permeable sensitive layer is made of a crystalline powder with a crystal size from 0.1 micrometer to 80 micrometers.

4. Sensor as in claim 1, wherein the gas permeable sensitive layer is a crystalline powder whose pores in total have an internal surface from 100 to 1500 $m^2$ per g powder.

5. Sensor as in claim 1, wherein the gas permeable sensitive layer is a crystalline powder with primary pores between 0.1 and 1.5 nm.

6. Sensor as in claim 1, wherein the gas permeable sensitive layer is a zeolite.

7. Sensor as in claim 6, wherein the zeolite is doped with metal of a side group of the periodic system at a concentration from 0.1 to 10% by weight.

8. Sensor as in claim 6, wherein the zeolite doping element is elemental or ionic metal or an oxide or a cluster.

9. Sensor as in claim 6, wherein the gas permeable sensitive layer is comprised from 50 to 100% of zeolite.

10. Sensor as in claim 6, wherein said zeolite has a crystal structure with pores, ducts and channels of a diameter between 0.1 and 1.5 nm.

11. Sensor as in claim 1, wherein said electric capacitor has an interdigitized construction as far as its electrodes are concerned.

12. Sensor as in claim 11 wherein the structural width of the electric capacitor is between 1 micrometer and 100 micrometer, and a thickness of about 2 micrometer.

13. Sensor as in claim 1, being constructed as a three dimensionally effective unit, the electric capacitor having electrodes being from 2 micrometers to 100 micrometers high.

14. Sensor as in claim 1, wherein said electric capacitor has electrodes being from 1 to 100 micrometers wide.

15. Sensor as in claim 1, including means for heating and sensing the gas permeable sensitive layer temperature.

* * * * *